United States Patent
Teles et al.

(10) Patent No.: US 6,712,942 B2
(45) Date of Patent: Mar. 30, 2004

(54) WORKING UP A MIXTURE COMPRISING ALKENE AND OXYGEN

(75) Inventors: Joaquim Henrique Teles, Otterstadt (DE); Alwin Rehfinger, Mutterstadt (DE); Peter Bassler, Viernheim (DE); Norbert Rieber, Mannheim (DE); Werner Hefner, Lampertheim (DE); Anne Wenzel, Eggenstein-Leopoldshafen (DE); Peter Rudolf, Ladenburg (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 102 days.

(21) Appl. No.: 10/169,102

(22) PCT Filed: Jan. 12, 2001

(86) PCT No.: PCT/EP01/00347
§ 371 (c)(1),
(2), (4) Date: Jul. 12, 2002

(87) PCT Pub. No.: WO01/51475
PCT Pub. Date: Jul. 19, 2001

(65) Prior Publication Data
US 2003/0004387 A1 Jan. 2, 2003

(30) Foreign Application Priority Data
Jan. 14, 2000 (DE) .......................... 100 01 401

(51) Int. Cl.$^7$ .......................... B01D 31/40; B01D 31/14; C07D 301/32
(52) U.S. Cl. .............................. 203/29; 203/46; 549/541
(58) Field of Search ..................... 203/29, 46; 210/639; 549/541

(56) References Cited

U.S. PATENT DOCUMENTS

| 4,734,273 A | 3/1988 | Haskell |
| 4,939,286 A | 7/1990 | Brazdil et al. |
| 5,117,012 A | 5/1992 | Stavinoha et al. |
| 5,463,090 A | 10/1995 | Rodriguez et al. |

FOREIGN PATENT DOCUMENTS

| EP | 0 261 264 | 3/1988 |
| EP | 0 719 766 | 7/1996 |
| FR | 1 487 588 | 10/1967 |

*Primary Examiner*—Taofiq A Solola
(74) *Attorney, Agent, or Firm*—Oblon, Spivak, McClelland, Maier & Neustadt, P.C.

(57) ABSTRACT

A mixture (M1) comprising an alkene and oxygen is worked up by a process in which (i) oxygen is removed from the mixture (M1) by a nondistillative method to give a mixture (M2) and (ii) the alkene is separated off from the mixture (M2) by distillation.

8 Claims, No Drawings

WORKING UP A MIXTURE COMPRISING ALKENE AND OXYGEN

This application is a 371 of PCT/EP01/00347 filed Jan. 12, 2001.

FIELD OF INVENTION

The present invention relates to a process for working up a mixture which contains at least one alkene and oxygen, the oxygen being removed from the mixture by a suitable method before the alkene is separated off by distillation. The present invention also relates to an integrated process in which propylene oxide is prepared from a hydroperoxide, preferably hydrogen peroxide, and propene, the resulting mixture containing propene and oxygen and being worked up by the novel process.

BACKGROUND INFORMATION

In processes in which mixtures of an alkene and oxygen are obtained, it is desirable in numerous procedures to separate off the alkene from this mixture and, if required, to recycle it to a process stage for economic reasons relating to the process. One problem encountered in these processes is the formation of ignitable mixtures, which of course have to be avoided in all circumstances for safety reasons.

A process in which this problem occurs in particular is the preparation of propylene oxide, an important intermediate in the chemical industry, starting from propene and hydrogen peroxide. In the course of working up the product, in this process unconverted propene is preferably separated off from the crude discharge of the epoxidation and is recycled to the process as starting material. In one possible embodiment, this crude discharge is subjected to a distillation, after which the crude product is separated into a low boiler fraction, which contains propene and compounds having a boiling point lower than that of propene, and a high boiler fraction, which contains propene oxide and compounds having a boiling point higher than that of propene. Inter alia, oxygen collects in this low boiler fraction, in a concentration which makes the low boiler fraction an ignitable mixture which constitutes a serious safety risk. The risk is all the more important because, as described above, one process requirement is that unconverted propene be recycled and hence the low boiler fraction in turn be worked up, for example by distillation.

In order to solve this problem, EP-B 0 719 768 proposes adding an inert substance having a boiling point which is lower than that of propene, preferably methane, during the separation of propene from the low boiler mixture by distillation, in the upper part of the separation apparatus, in an amount such that the oxygen is diluted to a concentration at which the mixture is no longer ignitable. In this procedure, the dilution component accordingly has to be added to the separation apparatus, it also being necessary to add a solvent by means of which the propene is washed out of the low boiler fraction.

BRIEF SUMMARY

It is the object of the present invention to provide a process which makes it possible to work up mixtures which comprise alkene and oxygen in a simple and safe manner.

We have found that this object is achieved by a process for working up a mixture (M1), comprising an alkene and oxygen, in which (i) oxygen is removed from the mixture (M1) by a nondistillative method to give a mixture (M2) and (ii) the alkene is separated off from the mixture (M2) by distillation.

In a preferred embodiment, the mixture (M1) worked up by the novel process is a gaseous mixture.

Of course, the mixture (M1) may also contain two or more alkenes differing from one another. In this case, it is possible, inter alia, for one or more of the alkenes to be converted into one or more other compounds during the removal of the oxygen, provided that it is ensured that the desired alkene is present in the mixture (M2).

DETAILED DESCRIPTION OF THE INVENTION

In general, there are no restrictions with regard to the nondistillative methods by means of which oxygen is removed from the mixture (M1), provided that it is ensured that, during this removal, the alkene which is contained in the mixture (M1) and which is to be contained in the mixture (M2) is not converted to a significant extent into an undesirable product.

In the novel process, oxygen is preferably removed by combustion. Another preferred embodiment is one in which the mixture (M1) is subjected to reaction conditions under which the oxygen contained in the mixture reacts with a suitable chemical compound.

Accordingly, the present invention also relates to a process, as described above, wherein (i) oxygen is removed from the mixture (M1)

by combustion of the oxygen or by reaction of the oxygen contained in the mixture (M1) with at least one suitable chemical compound or by a combination of these methods.

Regarding the combination of the methods described above, it is in principle possible to use the two methods simultaneously in the case of suitable reactants, so that the oxygen is combusted as well as being consumed by reaction with a suitable compound. It is also possible for the two different procedures to be carried out in succession in any desired order, it being possible for each method also to be carried out two or more times.

Regarding the combustion, all possible procedures are possible in principle, provided that it is ensured that the alkene which is present in the mixture (M1) does not react to give undesirable products. Inter alia, the combustion of oxygen can be effected without using a catalyst. This noncatalytic combustion can be carried out using all reactors suitable for this purpose. For example, temperatures of more than 300° C. and pressures in the region of atmospheric pressure are preferably employed, the reactors used being, for example, tubular reactors with, for example, an inert bed.

In a preferred embodiment of the novel process, the combustion of the oxygen which is contained in the mixture (M1) is carried out using at least one suitable catalyst. All suitable catalysts or catalyst mixtures may be used for this purpose. Inter alia, noble metals, for example Pt, Rh or Pd, which may be applied to suitable supports, for example metal oxides, are preferred. For example, Pd catalysts supported on $Al_2O_3$ are used. Copper chromite catalysts may also be mentioned. Examples here include the commercially available catalysts R0-25/50 S6, R0-20/47 K2-4 or R3-20 S6 from BASF AG.

The temperatures which are used in the catalytic combustion of the oxygen which is contained in the mixture (M1) can be adapted to the requirements of the respective process, in particular the composition of the mixture (M1) and the type of catalyst used. In general, the temperatures are from 200 to 650° C., preferably from 280 to 580° C.

Regarding the reactor or the reactors in which the catalytic combustion takes place, all suitable reactors may be used. Examples of preferred reactors include tubular reactors, such as tube-bundle reactors or shaft reactors The residence time of the mixture (M1) in the reactors described above, under the reaction conditions described above, can be adapted to the requirements of the respective process. The amount of oxygen which is removed from the mixture (M1) can be influenced by, inter alia, the specific choice of the residence time. For example, it is possible that the mixture (M2) which is obtained after combustion of oxygen which is present in the mixture (M1) should or can still contain a specific residual amount of oxygen, which is not critical for any further working up of the mixture (M2). For economic reasons relating to the process, it is therefore possible in principle for the mixture (M2) to have a certain residual oxygen concentration.

As stated above, it is possible for the oxygen to be removed from the mixture (M1) in two or more stages by combustion. Thus, it is possible, inter alia, for oxygen to be removed from the mixture (M1) by combustion in a first stage using a first catalyst and for oxygen to be removed from the resulting mixture using a second catalyst, it being possible for the reaction conditions in the first and the second stage to be identical to or different from one another, for example with respect to temperature or residence time of the respective reaction medium in the reactor. Furthermore, the different stages can be carried out in one reactor or in a plurality of identical or different reactors, which may be tailored to the respective reaction conditions.

The catalytic combustion of the oxygen has, inter alia, the advantage that the temperatures to be used at the start of the combustion reaction are lower than in the case of the noncatalytic combustion.

In a further embodiment of the novel process, oxygen is removed from the mixture (M1) by reaction of the oxygen with a suitable chemical compound.

Here, the suitable chemical compound may be added, for example, to the mixture (M1) and reacted under suitable reaction conditions with the oxygen contained in the mixture (M1). It is of course also possible here to add two or more suitable compounds which are reacted with the oxygen. The compound resulting from this reaction or the resulting compounds may either remain in the mixture or be removed from the mixture, depending on the procedure.

Furthermore, the one or more suitable compounds which are reacted with the oxygen contained in the mixture (M1) may already be present in the mixture (M1). Of course, the one or more compounds may already be present in the mixture (M1) and the concentration of these compounds in the mixture may be increased by further addition of these compounds. The amount of compound which is additionally introduced may be adapted here, for example, to the amount of oxygen which is to be reacted or may be adapted to the reaction conditions under which the reaction with the oxygen is effected.

While in principle reactions which take place without the use of a catalyst are also possible for this reaction of the oxygen with at least one suitable compound, catalyzed reactions are preferred.

The present invention therefore also relates to a process, as described above, wherein the combustion of the oxygen or the reaction of the oxygen contained in the mixture (M1) with at least one suitable chemical compound is carried out catalytically.

Examples of reactants for oxygen, which are added to the mixture (M1) or are already present in the mixture (M1), are in principle all compounds which are capable of reacting with oxygen and which do not adversely affect the separation of the alkene from the mixture (M1) by distillation. In particular, the reaction product or the reaction products of the one or more compounds and oxygen may remain in the mixture or may be removed from the mixture (M1) by a suitable process before the alkene is separated off by distillation.

In a particularly preferred embodiment, mixtures (M1) which, in addition to oxygen and alkene, comprise an alkane corresponding to this alkene are used in the novel process. In the context of the present invention, the term alkane corresponding to an alkene denotes an alkane in which the one or more C—C double bonds present in the alkene are present as saturated C—C single bonds.

Accordingly, the present invention also relates to a process, as described above, wherein the mixture (M1) additionally comprises an alkane corresponding to the alkene.

Regarding the removal, described above, of oxygen from the mixture (M1), procedures in which the alkane contained in the mixture (M1) reacts with oxygen are particularly preferably to be mentioned here. In a particularly preferred embodiment, the alkane undergoes oxydehydrogenation with formation of the alkene corresponding to the alkane.

Accordingly, the present invention also relates to a process, as described above, wherein the oxygen is removed from the mixture (M1) according to (i) by oxydehydrogenation of the alkane to give the alkene. Of course, it is possible here for the mixture to contain at least one further alkane which does not correspond to the alkene contained in the mixture and which undergoes oxydehydrogenation to give the corresponding alkene. The mixture (M1) may also contain two or more alkenes and the alkanes corresponding to them, and the alkanes may be converted into the corresponding alkenes by oxydehydrogenation with removal of oxygen.

For the purposes of the present invention, the following alkane/alkene pairs are particularly preferred, it being possible for the alkane to be converted into the alkene by oxydehydrogenation with removal of oxygen: Propane/propene, ethane/ethene, ethylbenzene/styrene, cyclohexane/cyclohexene, cyclohexene/cyclohexadiene, cyclohexadiene/benzene, cyclopentane/cyclopentene.

The oxydehydrogenation of the one or more alkanes can be effected both catalytically and noncatalytically. Preferably, however, the oxydehydrogenation is carried out using a suitable catalyst. Regarding these catalysts, reference may be made, for example, inter alia to M. Xu, J. H. Lunsford, React. Kinet. Catal. Lett. 57 (1996), 3–11, and to B. Delmon, Stud. Surf. Sci. Catal. 110 (1997), 43–59, and to the literature cited therein, which are hereby fully incorporated by reference in the context of the present application.

In a particularly preferred embodiment of the present invention, a mixture (M1) which comprises propene, propane and oxygen is used, particularly preferably the propane being converted into propene by oxydehydrogenation with consumption of oxygen. An advantage here is that the removal of oxygen gives a product which is already contained in the mixture (M1) and is separated off by distillation according to (ii).

The present invention hence also relates to a process, as described above, wherein the mixture (M1) comprises propene, propane and oxygen.

As stated above, the oxygen can also be removed from the mixture comprising propane, propene and oxygen by non-catalytic combustion or, preferably, by catalytic combustion.

The oxygen can also be removed both by combustion and by oxydehydrogenation of the propane. In particular, the two processes can also be combined in a suitable manner, for example by carrying out oxydehydrogenation of propane to propene in at least one step and removing oxygen from the mixture (M1) by combustion in at least one further step, which can be effected before or after the oxydehydrogenation. Furthermore, oxydehydrogenation and combustion can also be carried out simultaneously.

All suitable catalysts may be used in the removal of oxygen from the mixture (M1) by oxydehydrogenation of propane. In particular, catalysts described in the abovementioned articles by M. Xu and B. Delmon may be mentioned here.

Depending on the amount of oxygen contained in the mixture (M1), the amount of propane contained in the mixture (M1) or the amount of oxygen which is to be contained in the resulting mixture (M2), it may be necessary to add further propane to the mixture (M1), in addition to the propane which is already contained in the mixture (M1) and which, for example, originates from an upstream process stage.

For the purposes of the novel process, it is possible to remove oxygen from mixtures (M1) which have substantially any oxygen content.

For the purposes of the novel process, it is possible, for example, to add alkane to the mixture (M1) in a controlled manner in order to remove the desired amount of oxygen by oxydehydrogenation.

By means of the methods as described above for oxygen removal, it is possible to reduce the oxygen concentration in the mixture (M1) to any desired value which is required by the further use or the further working-up of the resulting mixture (M2). With particular preference, for example, when reducing the oxygen content of a mixture comprising propene, propane and oxygen, oxygen contents of the low boiler fraction of the mixture (M2) of 12% by volume or less are preferred and an oxygen content of 8% by volume or less is particularly preferred. In the context of the present invention, the term low boiler fraction of the mixture (M2) denotes the fraction of those compounds of the mixture (M2) which have a boiling point which is lower than the boiling point of the alkene, for example propene. Here, the abovementioned data in % by volume are based on the total volume of the total low boiler fraction of the mixture (M2).

The present invention therefore also relates to a process, as described above, wherein the low boiler fraction of the mixture (M2) contains 8% by volume of oxygen or less.

After oxygen has been removed from the mixture (M1) in at least one stage according to at least one process as described above, it is possible, if required, to bring the mixture (M2) into contact with at least one suitable solid before the alkene is separated off by distillation according to (ii) in at least one further step, this solid having reducing properties and being capable of further reducing the oxygen content of the mixture (M2).

All suitable solids which have this reducing property may be used. Examples are, inter alia, readily oxidizable metals, for example alkali metals, alkaline earth metals, rare earth metals, Cu, Al, Zn and cadmium. These are preferably used, for example, in a form applied to a suitable inert support. For example, the solid R3-11G T5×3, a finely divided copper on magnesium silicate, commercially available from BASF, is particularly preferred.

The present invention therefore also relates to a process, as described above, wherein, before the alkene is separated off by distillation, the mixture (M2) is brought into contact with a solid, by means of which oxygen present in the mixture (M2) is reduced.

This bringing into contact is very particularly preferably carried out in a gas-phase reaction, the reaction temperature employed preferably being from room temperature to 250° C. Pressures of up to 30 bar are preferably employed, and the throughput is preferably more than 1000, particularly preferably more than 1000 to 3000, $m^3(S.T.P.)/(m^3 \cdot h)$. In principle, any suitable reactor may be used. Tubular reactors or shaft reactors are preferred here.

The one or more solids stated can of course be brought into contact with the mixture (M1) during the removal of oxygen from the mixture (M1) by combustion or by reaction of the oxygen with a suitable compound, for example preferably by oxydehydrogenation of an alkane.

The low boiler fraction of the mixture (M2), whose oxygen content was reduced by the methods as described above, has, as described above, an oxygen concentration which is in general in the region of 12% by volume or less, preferably 8% by volume or less, based on the total volume of the low boiler fraction of (M2).

After the removal of oxygen from the mixture (M1) to give the mixture (M2), from which further oxygen can be removed by bringing into contact with a suitable solid, as described above, the one or more alkenes are removed from the mixture (M2) by distillation. Regarding the one or more distillation steps mentioned, all procedures are possible, in particular those known from the prior art.

In general, oxygen can be removed from all suitable mixtures (M1) as described above by the novel process. In a very particularly preferred embodiment, mixtures (M1) which result from the preparation of an alkene oxide, starting from alkene and a hydroperoxide, are worked up, this epoxidation furthermore particularly preferably being carried out in the presence of a catalyst based on a zeolite, preferably a titanium silicalite.

Zeolites per se are known to be crystalline aluminosilicates having ordered channel and cage structures which have micropores. The term micropores as used in the context of the present invention corresponds to the definition in Pure Appl. Chem. 57 (1985), 603–619, and denotes pores having a pore diameter of less than 2 nm. The network of such zeolites is composed of $SiO_4$ and $AlO_4$ tetrahedra, which are linked via common oxygen bridges. An overview of the known structures is to be found, for example, in W. N. Meier, D. H. Olson and Ch. Baerlocher, Atlas of Zeolite Structure Types, Elsevier, 4th Edition, London 1996.

In particular there are zeolites which contain no aluminum and in which some of the Si(IV) in the silicate lattice has been replaced by titanium in the form of Ti(IV). The titanium zeolites, in particular those having a crystal structure of the MFI type, and possibilities for their preparation are described, for example, in EP-A 0 311 983 or EP-A 0 405 978.

Titanium zeolites having an MFI structure are known to be identifiable by a specific pattern in their determination by X-ray diffraction and additionally from a skeletal vibration band in the infrared range (IR) at about 960 $cm^{-1}$ and thus differ from alkali metal titanates or crystalline or amorphous $TiO_2$ phases.

Specific examples are zeolites having a pentasil zeolite structure, in particular the types assigned by X-ray diffraction to the BEA, MOR, MWW, RUT, RTH, EUO, FER, FAU, LTA, MTT, MTW, CHA, AFI, ERI, SOD, RHO, BOG, NON, EMT, MTN, HEU, DDR, DOH, LTL, NES, KFI, RSN, SGT, MFS, MFI or MEL structure or to a mixed structure comprising MFI and MEL. A plurality of these zeolites of this type are described, for example, in the abovementioned publication by Meier et al.

Accordingly, the present invention also relates to an oxide material, as described above, wherein the zeolite structure is selected from the group consisting of MFI, MEL, BEA, MOR, MWW, RUT, RTH, EUO, FER, FAU, LTA, MTT, MTW, CHA, AFI, ERI, SOD, RHO, BOG, NON, EMT, MTN, HEU, DDR, DOH, LTL, NES, KFI, RSN, SGT, MFS, MTF and a mixed structure comprising two or more thereof.

In general, the zeolite catalyst, preferably titanium silicalite catalyst, is prepared in a process which comprises at least one crystallization step. Typically, for example, the abovementioned titanium silicalites are prepared by reacting an aqueous mixture of an $SiO_2$ source, a titanium oxide and a nitrogen-containing organic base, e.g. tetrapropylammonium hydroxide, in the presence or absence of an alkali solution, in a pressure-resistant container at elevated temperatures for several hours or a few days, a crystalline product being obtained. This is, as a rule, filtered off, washed, dried and calcined at elevated temperatures to remove the nitrogen-containing organic base. In the powder thus obtained, the titanium is present at least partly within the zeolite framework in varying amounts with four-, five- or six-fold coordination (Behrens et al., J. Chem. Soc., Chem. Commun. (1991), 678–680). This may be followed by repeated washing with a hydrogen peroxide solution containing sulfuric acid, after which the titanium zeolite powder has to be dried again and calcined, as described, for example, in EP-A-0 276 362. The above-described crystallization of the zeolite from suitable starting materials by hydrothermal reaction is carried out in general at from 50 to 250° C. over a sufficiently long period, autogenous pressure being established in a temperature-dependent manner. Depending on the procedure, the zeolite obtained, preferably the titanium silicalite obtained, can then be used for the epoxidation either in the form of a powder or in the form of a molding.

All suitable methods may be used for the preparation of a molding. In the molding step, one or more viscosity-enhancing substances may be added as a pasting agent. All suitable substances known from the prior art may be used for this purpose. In the novel process, water and mixtures of water with one or more water-miscible organic substances are preferably used as pasting agents. The pasting agent may be removed during the subsequent calcination of the molding.

Organic, in particular hydrophilic organic polymers, e.g. cellulose, cellulose derivatives, such as methylcellulose, ethylcellulose or hexylcellulose, polyvinylpyrrolidone, ammonium (meth)acrylates, tylose or mixtures of two or more thereof are preferably used. Methylcellulose is particularly preferably used.

Ammonia, amines or amine-like compounds, e.g. tetraalkylammonium compounds or aminoalcoholates, may be added as further additives. Such further additives are described in EP-A 0 389 041, EP-A 0 200 260 and WO 95/19222, which are hereby fully incorporated by reference in the context of the present application.

Instead of basic additives, it is also possible to use acidic additives. Organic acidic compounds which can be burnt out by calcination after the molding step are preferred. Carboxylic acids are particularly preferred.

The amount of these assistants is preferably from 1 to 40, particularly preferably from 2 to 25,% by weight, based in each case on the molding finally prepared, as described below.

In order to influence the properties of the molding, for example transport pore volume, transport pore diameter and transport pore distribution, further substances, preferably organic compounds, in particular organic polymers, can be added as further additives which can also influence the moldability of the material. Such additives include alginates, polyvinylpyrrolidones, starch, cellulose, polyethers, polyesters, polyamides, polyamines, polyimines, polyalkenes, polystyrenes, styrene copolymers, polyacrylates, polymethacrylates, fatty acids, for example stearic acid, high molecular weight polyalkylene glycols, for example polyethylene glycol, polypropylene glycol or polybutylene glycol, or mixtures of two or more thereof. Other examples are acrylate-based polymer dispersions, melamine resins, phenol resins and polyurethanes. Those compounds which, after the preparation of the molding, can be completely removed from the molding by drying and/or calcination steps in a suitable atmosphere and at elevated temperatures are preferably used.

The mixture can be compacted in a suitable manner before the actual molding, if desired the generally still pulverulent mixture being homogenized for from 10 to 180 minutes in a kneader or extruder prior to compaction. As a rule, temperatures of from about 10° C. to the boiling point of the pasting agent and atmospheric pressure or slightly superatmospheric pressure are employed. The mixture is kneaded until an extrudable material has formed.

In principle, kneading and molding can be effected using all conventional kneading and molding apparatuses or processes, as known in large numbers from the prior art and suitable for the preparation of, for example, catalyst moldings.

Preferably used processes are those in which the molding is effected by extrusion in conventional extruders, for example to give extrudates having a diameter of usually from about 1 to about 10 mm, in particular from about 1.5 to about 5 mm. Such extrusion apparatuses are described, for example, in Ullmann's Enzyklopädie der Technischen Chemie, 4th Edition, Vol. 2 (1972), page 295 et seq. In addition to the use of an extruder, an extrusion press is also preferably used.

By choosing suitable dies, the geometric shape of the molding, in particular the extrudate diameter and the cross-sectional shape, can be influenced. The latter can be widely varied by preparing, for example, honeycomb, clover leaf, wagon wheel, star, hollow strand or other shapes. By agglomeration methods, the molding can also be prepared in the form of spheres of variable diameter in the novel process.

The extrudates are either strands or honeycomb elements. The honeycombs may have any desired shape. They may comprise, for example, round strands, hollow strands or star-shaped strands. Furthermore, the honeycombs may have any desired diameter. The external shape and the diameter are as a rule determined by the process engineering requirements which are prescribed by the process in which the molding is to be used.

After the end of the extrusion, the moldings obtained are dried at, in general, from 50 to 250° C., preferably from 80 to 250° C., at in general from 0.01 to 5, preferably from 0.05 to 1.5, bar in the course of from about 1 to 20 hours.

In a preferred embodiment, the oxide material, regardless of whether it is in the form of moldings or powder, is calcined before the further reaction according to (b). This subsequent calcination is effected at temperatures of in general from room temperature to 1200° C., preferably from 300 to 800° C., particularly preferably from 450 to 700° C. The pressure range is chosen similarly to that of the drying.

The calcination takes place in an oxidizing or reducing atmosphere As a rule, calcination is effected in an oxygen-containing atmosphere, the oxygen content being from 0.1 to 90, preferably from 0.2 to 22, particularly preferably from 0.2 to 10,% by volume. When the oxide material is used as a catalyst, the duration of the calcination can be adapted in such a way that, for example, a desired combination of catalytic activity and mechanical stability is achieved.

Of course, the extrudates described above can be subjected to a finishing step. All comminution methods are possible, for example by splitting or breaking the moldings, as well as further chemical treatments, for example as described above. If comminution takes place, granules or chips having a particle diameter of from 0.1 to 5 mm, in particular from 0.5 to 2 mm, are preferably produced.

These granules or these chips and also moldings produced by another method contain virtually no fractions having particles finer than those with a minimum particle diameter of about 0.1 mm.

Particularly preferably, one or more of the alkenes mentioned below are used as the alkene which is epoxidized:

Ethene, propene, 1-butene, 2-butene, isobutene, butadiene, pentenes, piperylene, hexenes, hexadienes, heptenes, octenes, diisobutene, trimethylpentene, nonenes, dodecene, tridecene, tetra- to eicosenes, tri- and tetrapropene, polybutadienes, polyisobutenes, isoprenes, terpenes, geraniol, linalool, linalyl acetate, methylenecyclopropane, cyclopentene, cyclohexene, norbornene, cycloheptene, vinylcyclohexane, vinyloxirane, vinylcyclohexene, styrene, cyclooctene, cyclooctadiene, vinylnorbornene, indene, tetrahydroindene, methylstyrene, dicyclopentadiene, divinylbenzene, cyclododecene, cyclododecatriene, stilbene, diphenylbutadiene, vitamin A, beta-carotene, vinylidene fluoride, allyl halides, crotyl chloride, methallyl chloride, dichlorobutene, allyl alcohol, methallyl alcohol, butenols, butenediols, cyclopentenediols, pentenols, octadienols, tridecenols, unsaturated steroids, ethoxyethene, isoeugenol, anethole, unsaturated carboxylic acids, e.g. acrylic acid, methacrylic acid, crotonic acid, maleic acid or vinylacetic acid, unsaturated fatty acids, e.g. oleic acid, linoleic acid, palmitic acid and naturally occurring fats and oils.

Preferably alkenes of 2 to 8 carbon atoms, particularly preferably ethene, propene or butene, in particular propene, are suitable for the epoxidation. The hydroperoxide used for the purpose of the present invention is particularly preferably hydrogen peroxide.

Here, a mixture which contains alkene oxide, solvent and unconverted alkene as well as oxygen and further compounds which have a boiling point which is below that of the alkene oxide is preferably formed in the epoxidation. Particularly in the case of the epoxidation of propene, the propene used has, depending on the purity, a propane content of up to 30% by weight, based on the sum of propene and propane. Accordingly, the mixture which forms as crude discharge from the epoxidation of propene also contains a certain amount of propane.

The present invention therefore also relates to an integrated process for the preparation of propylene oxide, in which (a) propene and hydrogen peroxide, in a solvent, are reacted in the presence of a zeolite catalyst, preferably a titanium silicalite catalyst, to give propylene oxide, a mixture (M0) being obtained, (b) the mixture (M0) which results from (a) and comprises propylene oxide, solvent, unconverted propene, propane contained in the propene starting material and oxygen and further chemical compounds which have a lower boiling point compared with propene is separated by distillation to give a mixture which essentially comprises propylene oxide and solvent, and a mixture (M1) is obtained which comprises essentially propene, propane, oxygen and the further chemical compounds which have a lower boiling point compared with propene, (c) oxygen is removed from the mixture (M1) by a catalytic process to give a mixture (M2) comprising propene, and (d) propene is separated off from the mixture (M2) by distillation and is recycled to (a).

An integrated process in which, after (c) but before (d), the mixture (M2) is brought into contact with a solid which reduces oxygen is likewise preferred. Regarding this solid, reference may be made to the embodiments described further above.

The mixture (M1), which consists of the low boiler components of the mixture (M0), has a propane content of from 0.5 to 85% by volume, depending on the propane content of the propene used, as described above.

Further components which may be mentioned which are contained in the mixture (M1) in the integrated process described above include, in addition to oxygen, for example carbon dioxide, carbon monoxide, hydrogen or ethane, which either were contained in the propene used or are formed as byproducts of the epoxidation. The oxygen concentration of the mixture (M1) in this integrated process is in general in the region of up to 11% by volume.

In a further preferred embodiment, the present invention also relates to an integrated process, as described above, wherein the catalytic process according to (c) is the catalytic oxydehydrogenation of the propane contained in (M1) to give propene, or the catalytic combustion of the oxygen, the catalyst used being a $Pd/Al_2O_3$ catalyst, or a combination of these methods.

The propene separated off by distillation according to (d) can, if required, also be subjected to one or more purification stages before being recycled as a starting material to (a), all processes known from the prior art being possible here.

In a further possible embodiment of the novel process, a part of the stream (M1) can be removed from the process and, for example, fed to one or more other processes. It is also possible to recombine that part of the stream (M1) which was removed from the process with the stream (M2) which results from that part of the stream (M1) which was not removed and from which the oxygen was removed by one of the methods described above, and to separate off alkene in a manner corresponding to (d) from the resulting product stream by distillation.

The Examples which follow illustrate the invention.

EXAMPLES

Example 1

Epoxidation of Propene 40 g of methanol, 5.6 g of TS-1 catalyst powder, prepared as described, for example, in DE-A 41 38 155, and 7.8 g of propene (chemical grade, 95% by volume of propene and 5% by volume of propane) were initially taken in a stirred autoclave having a capacity of 120 ml.

The mixture was cooled to 23° C. 7.7 g of a commercial 50% strength solution of hydrogen peroxide were then added in one portion to the mixture, the temperature increasing to 150° C. and the pressure to 19 bar.

After the reaction had ended, the autoclave was cooled to 20° C. and the gas phase was investigated by means of gas chromatography. It had the following composition:

| | |
|---|---|
| Propene: | 64.1% by volume |
| Propane: | 7.5% by volume |
| Oxygen: | 24.9% by volume |
| $CO_2$: | 0.7% by volume |
| CO: | 0.08% by volume |
| $H_2$: | 0.3% by volume |

Example 2

Epoxidation of Propene

Example 1 was repeated with the following modifications:

The metering of the hydrogen peroxide and the cooling were adjusted so that the reaction temperature did not exceed 35° C. After the reaction had ended, the autoclave was cooled to 20° C. and the gas phase was investigated by means of gas chromatography. It had the following composition:

| | |
|---|---|
| Propene: | 44.1% by volume |
| Propane: | 51.0% by volume |
| Oxygen: | 0.6% by volume |
| $CO_2$: | 0.01% by volume |
| CO: | <0.01% by volume |
| $H_2$: | <0.01% by volume |

Example 3

Reaction of the Gas Mixture from Example 2 with a Propene Oxyde-hydrogenation Catalyst The oxydehydrogenation catalyst ($LiCl/TiO_2$) was prepared as stated in Xu, Lunsford, React. Kinet. Catal. Lett. 57 (1996), 3–11. The supports used were premolded $TiO_2$ (99% rutile) extrudates having a diameter of 2 mm. A tubular reactor (length=24 cm, diameter=12 mm) was filled with catalyst chips (about 1 mm) and heated to 585° C. under a stream of nitrogen.

After the reaction temperature had been reached, the nitrogen was shut off and a gas mixture having a composition as in Example 2 was passed through the reaction at 500 ml/min under atmospheric pressure (corresponds to an empty tube residence time of about 3 seconds).

After one hour, a sample of the gaseous reactor discharge was investigated by means of gas chromatography. The mixture had the following composition:

| | |
|---|---|
| Propene: | 47.4% by volume |
| Propane: | 46.9% by volume |
| Oxygen: | 0.01% by volume |
| $CO_2$: | 0.4% by volume |
| CO: | 0.3% by volume |
| $H_2$: | <0.01% by volume |
| Methane: | 0.5% by volume |
| Ethane: | 1.9% by volume |

The concentration of oxygen in the mixture, which contains all components having a boiling point below the boiling point of propene, was now only 0.3% by volume. Safe distillation of this gas mixture for recycling of the propene is thus possible.

Example 4

Reaction of the Gas Mixture from Example 2 with a Combustion Catalyst

The reactor from Example 3 was filled with a commercial combustion catalyst based on palladium (0.5% by weight) on a gamma-$Al_2O_3$ support in the form of spheres having a diameter of about 2 mm. The reactor was heated to 350° C. under a stream of nitrogen. Thereafter, the stream of nitrogen was shut off and a gas mixture having the composition stated in Example 2 was passed through the catalyst (flow rate=500 ml/min at atmospheric pressure). The reactor heating was regulated so that the exit temperature of the gas mixture was about 350° C. After operation for 1 hour, the gas mixture emerging from the reactor was analyzed by gas chromatography. The mixture had the following composition:

| | |
|---|---|
| Propene: | 49.6% by volume |
| Propane: | 40.1% by volume |
| Oxygen: | 0.009% by volume |
| $CO_2$: | 0.1% by volume |
| CO: | 0.9% by volume |
| $H_2$: | <0.01% by volume |
| Methane: | 1.5% by volume |
| Ethane: | 3.4% by volume |

The concentration of oxygen in the mixture, which contained all components having a boiling point below the boiling point of propene, was now only 0.2% by volume. Safe distillation of this gas mixture for recycling of the propene is thus possible.

We claim:

1. A process for working up a discharge mixture (M1), comprising an alkene and oxygen, in which (i) oxygen is removed from the mixture (M1) by a nondistillative method to give a mixture (M2) and (ii) the alkene is separated off from the mixture (M2) by distillation.

2. A process as claimed in claim 1, wherein, according to (i), oxygen is removed from the mixture (M1)

by combustion of the oxygen or by reaction of the oxygen contained in the mixture (M1) with at least one suitable chemical compound or by a combination of these methods.

3. A process as claimed in claim 2, wherein the combustion or the reaction of the oxygen contained in the mixture (M1) with at least one suitable chemical compound is effected catalytically.

4. A process as claimed in claim 1, wherein the mixture (M1) additionally comprises an alkane corresponding to the alkene.

5. A process as claimed in claim 4, wherein the oxygen is removed from the mixture (M1) according to (i) by oxydehydrogenation of the alkane to give the alkene.

6. A process as claimed in claim 4, wherein the mixture (M1) comprises propene, propane and oxygen.

7. A process as claimed in claim 6, wherein the mixture (M2) contains 8% by volume of oxygen or less.

8. A process as claimed in claim 7, wherein, before the alkene is separated off by distillation, the mixture (M2) is brought into contact with a solid, by means of which the oxygen present in the mixture (M2) is reduced.

* * * * *